United States Patent [19]
Maddock

[11] Patent Number: 5,474,772
[45] Date of Patent: Dec. 12, 1995

[54] METHOD OF TREATMENT WITH MEDICAL AGENTS

[75] Inventor: Stephen W. Maddock, Lakewood, Colo.

[73] Assignee: Cobe Laboratories, Inc., Arvada, Colo.

[21] Appl. No.: 562,009

[22] Filed: Aug. 2, 1990

Related U.S. Application Data

[63] Continuation-in-part of Ser. No. 388,664, Aug. 2, 1989, abandoned.

[51] Int. Cl.$^6$ .................................................. A61K 39/00
[52] U.S. Cl. ................................ 424/140.1; 604/5; 604/6; 604/28
[58] Field of Search ........................... 424/85.91, 140.1; 604/5, 6, 28

[56] References Cited

U.S. PATENT DOCUMENTS

| | | | |
|---|---|---|---|
| 4,215,688 | 8/1980 | Terman et al. | 128/214 |
| 4,223,672 | 9/1980 | Terman et al. | 128/214 |
| 4,350,156 | 9/1982 | Malchesky et al. | 128/214 |
| 4,371,515 | 2/1983 | Chu | 436/544 |
| 4,687,808 | 9/1987 | Jarrett et al. | 525/54.1 |

OTHER PUBLICATIONS

Wahl et al., Intraperitoneal Delivery of Radiolabelled Monoclonal Antibodies: Effect of Peritoneal Lavage on Intraperitoneal Tumor Uptake. (1987) Journal of Nucl. Med. 28:715.
Strand et al., Plasmapheresis as a Tool for Enhancing Contrast in Radioimmunoimaging and Modifying Absorbed Doses in Radioimmunotherapy. (1989).
Norrgren et al., Evaluation of Extracorporeal Immunoadsorption in Radioimmunoimaging and Radioimmunotheraphy. (1990) Proceeds from the 3rd Conference vol. 4:54.
Ferrone et al., Improvement by Affinity Chromatography on Anti–idiotypic mAb . . . (1990) Proceeds from the 3rd Conference vol. 4:15.
Wahl, R. Overview: Experimental Targeting. (1990) Proceeds from the 3rd Conference vol. 4:15.
Henry et al., Improved Monoclonal Antibody Tumor/Background Ratios with Exchange Transfusions. (1990) Proceeds from the 3rd Conference vol. 4:22; Nucl. Med. Biol. (1991) 18:565–567.
Nilsson et al. Extracorporeal Immonoadsorption Therapy on Reats. In Vivo Depletion of Specific Antibodies. (1990) Clin. Exp. Immunol. 82:440–444.
Henry et al., Improved Monoclonal Antibody Tumor/Background Ratios with Exchange Transfusions. (1991) Nuc. Med. Biol. 18:565–567.
Wahl et al., Systemic Perfusion: A Method of Enhancing Relative Tumor Uptake of Radiolabeled Monoclonal Antibodies. (1988) Nuc. Med. Biol. 15:611–616.
Ingvar et al., Biokinetics of Radiolabeled Monoclonal Antibodies in Heterotransplanted Nude Rats: Evaluation of Corrected Specific Tissue Uptake. (1989) J. Nucl. Med. 30:1224–1234.
Norrgren et al., Contrast Enhancement in RII and Modification of the Therapeutic Ratio in RIT: A Theoretical Evaluation of Simulated Extracorporeal Immunoadsorption. (1992) Antibody, Immunoconjugates . . . 4:61–73.

*Primary Examiner*—Marianne M. Cintins
*Assistant Examiner*—Russell Travers
*Attorney, Agent, or Firm*—Beaton & Folsom

[57] ABSTRACT

A method of therapeutic or diagnostic treatment using a medical agent in which there will be beneficial effects if the level of circulating medical agent is reduced artificially faster than the reduction by the normal clearance or routes that obviate normal clearance mechanisms. The method includes the extracorporeal removal of the medical agent by passing bodily fluid from the patient over a support adapted to selectively immobilize the medical agent.

4 Claims, 1 Drawing Sheet

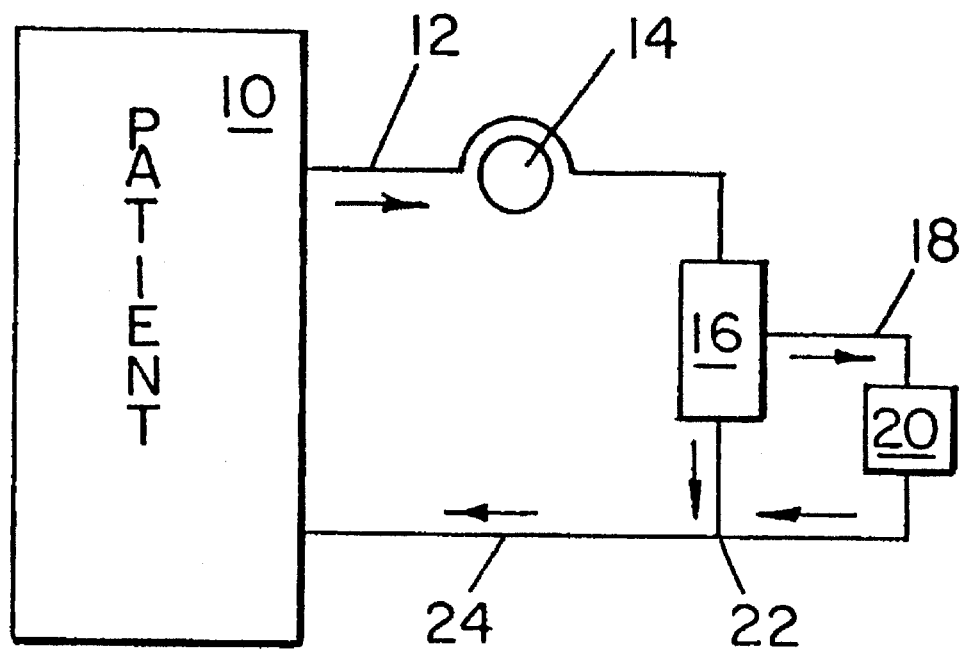

5,474,772

METHOD OF TREATMENT WITH MEDICAL AGENTS

CROSS-REFERENCE TO RELATED APPLICATION

This application is a continuation-in-part of application Ser. No. 07/388,664 filed Aug. 2, 1989, now abandoned.

FIELD OF THE INVENTION

This invention relates to the treatment of a patient with medical agents or therapeutic molecules that have short-term beneficial effects, and other, particularly longer-term, adverse effects.

BACKGROUND OF THE INVENTION

Many medical agents are administered to a patient for achieving a desired biological effect at one or more tissues. Often the therapeutic affect of the administered substance is accompanied by toxic effects. Toxic effects may be immediate or delayed, acute or chronic, or any combination of these. The toxic effects may include, but are not limited to, radiation exposure, immunization to the substance, alteration of normal metabolic function, specific tissue damage, and other diverse and/or idiosyncratic symptoms.

Medical agents are also administered for the purpose of diagnosing diseases. The time span during which the agents are effective for this purpose are often limited. The relative effectiveness of the administered agent as a diagnostic agent can also be limited by the relative specificity of targeting of that agent to specific tissues in the body. Removal of the administered substances can often enhance the effectiveness of the substance.

The present invention discloses a method for the treatment of a patient with a wide variety of medical agents for therapeutic or diagnostic purposes. The common element that defines the group of medical agents included within the scope of this invention is that they all, for a variety of reasons, reach a certain point in time after the initial treatment when their continued existence in the patient's body is no longer desireable, and is generally harmful. In some cases, the circulating medical agent is toxic to the body. In other circumstances, the medical agent itself is not toxic, but the bodies mechanism for clearing the agent may be harmful to the body. In many cases the agent will accumulate, in equilibrium with circulating concentrations of the agent, in certain tissues in the body. In these cases, the agents toxicity is localized to these tissues.

The method of the present invention encompasses the treatment of a patient with a medical agent and the subsequent selective extracorporeal removal of that agent from the patient's body. Although the extracorporeal removal of agents from patients is a well-known procedure, its combination within an integrated treatment scheme has heretofore not been described.

In a treatment scheme somewhat related to the method of the present invention, there has been described a procedure that begins with the introduction of foreign proteins into the body of a patient. These foreign, or exogenous, proteins may be immunotoxins that are introduced into the patient in order to immunologically attack an undesirable element in the patient's body. In time, the presence of the exogenous protein generates, via the patient's immune system, antibodies to the exogenous proteins. The presence of the antibodies will effectively neutralize the beneficial effects of the exogenous protein.

U.S. Pat. Nos. 4,865,841 and 4,801,449 of Balint, Jr. et al. and 4,215,688 of Terman et al. each describe a treatment procedure whereby the endogenously produced antibodies are removed from a patient via selective extracorporeal treatment. In each of these cases, an immunoadsorption column is prepared by covalently binding a material that will selectively immobilize the endogenous protein from the blood plasma. Since the endogenous protein which is to be removed is the antibody to the originally administered exogenous protein, selective immunoadsorption can be achieved by bonding the exogenous protein to the column material. The critical distinction between the present invention and the procedures described by Balint, Jr. and Terman is that in these procedures the agent or protein being selectively extracorporeally removed from the patient is not the same agent with which the patient is being treated, but an endogenously produced material generated by the body in response to the exogenous medical agent. Also see U.S. Pat. No. 4,838,852 of Edelson et al for a related system.

In U.S. Pat. Nos. 4,375,414, 4,620,977, 4,834,973 and 4,813,924 of Strahilevitz there is a described a procedure for the extracorporeal removal of psychoactive drugs from the blood stream. Again, immunoadsorption columns are described which will selectively remove the target drug from the blood stream in an extracorporeal manner. Although this procedure involves the extracorporeal removal of exogenous materials from a patient, it is not in any way part of an integrated treatment or diagnostic method. It is assumed that these methods are directed to the rescue of patients who have taken potentially harmful quantities of these non-therapeutic and non-diagnostic drugs.

U.S. Pat. Nos. 4,824,432, 4,605,394, and 4,362,155 of Skurkovich et al. describe methods for the treatment of pathological conditions connected with the production of interferons which destroy the immune system. In one embodiment, the endogenously produced interferons are removed by extracorporeal perfusion of a patient's blood. Again, these disclosures do not relate to an integrated treatment where medical agents are administered to a patient for therapeutic or diagnostic purposes and then removed from the patient by selective extracorporeal means in order to prevent harmful effects to the patient caused by the long-term presence of the exogenous agent. Also see U.S. Pat. No. 4,925,920 of Mannick et al.

In U.S. Pat. No. 4,800,016 of Yang, an extracorporeal system for the treatment of blood is described. The invention of the Yang patent is employed in medical procedures where blood is processed in an extracorporeal device, such as an artificial kidney or heart-lung machine, and the blood is heparinized to prevent clotting within the channels of the extracorporeal device. Traditionally, after heparin-containing blood has been treated in such extracorporeal devices protamine is added to the blood prior to its reintroduction into the body to negate the anti-coagulating effects of the heparin. In the Yang method, the heparin is selectively eliminated from the blood stream by passing it through a support that contains covalently-bonded protamine. By this means the heparin is actually removed from the bloodstream rather than just having its effects negated.

Yang differs from the present invention in that the heparin is not administered to a patient, but is merely part of the extracorporeal treatment of the patient's blood. The heparin does not provide a therapeutic or diagnostic benefit to the patient, but merely acts to facilitate the already extracorporeal blood supply treatment. A analogous method is described in U.S. Pat. No. 4,863,611 of Bernstein, et al., wherein heparinase, immobilized on agarose beads, is used to remove the heparin from the blood prior to its reintroduction into the patient.

The immobilization of immunochemicals for use in selective separation procedures is well known. Methods for the preparation of cellulose or agarose supports that contain covalently bonded molecules, such as antibodies, are commercially available. These immobilized materials have occasionally been used in extracorporeal systems for the removal of specific materials from blood plasma. See, for example, U.S. Pat. No. 4,846,786 of Freed et al.

A related technology is described in U.S. Pat. No. 4,877,599 of Lees. Lees describes a method for the detection of vascular disease by administering to a patient a conjugate diagnostic reagent. The conjugate reagent includes a target-seeking biologically active molecule and labelling means for extracorporeal detection. The method does not include the extracorporeal removal of the administered reagent.

In a similar scheme, U.S. Pat. No. 4,863,713 of Goodwin et al. describes a system for localizing a diagnostic or therapeutic agent to an internal target site. The system includes an epitopic compound, a binding protein that will direct the compound, and a clearing agent which will form a protein aggregate which is readily cleared from the patient's blood.

Extracorporeal systems for the treatment of bodily fluids are well known. In general, blood is removed from the patient and separated into plasma and blood concentrate streams. Extracorporeal treatment is almost always more effective when treating the plasma stream. After chemical modification or treatment is performed, the blood is returned to the patient.

There are several instances where the optimal treatment of a patient with a medical agent for therapeutic or diagnostic procedures would include artificial or extracorporeal rescue. Nearly all administered medical agents will ultimately be cleared from the body. Generally, compounds are cleared by the functions of the liver, spleen and kidneys and the reticuloendothelial system. However, clearance can also involve immunological immobilization and degradation. Some medical agents also will accumulate in certain tissues in the body for relatively long periods of time. This invention encompasses treatments with therapeutic or diagnostic agents wherein it would be desireable to remove or drastically diminish the amount of such agents from the body before the agents would be cleared by the body under normal circumstances.

One example of a suitable medical agent system is the administration of radiolabled antibodies to cancer patients for the purpose of diagnosing tumors and/or for therapeutic treatment of tumors. The treatments involve injection of a radiolabeled monoclonal anti-tumor antibody which has a binding specificity for molecules primarily restricted to tumor cells.

Conventional radiation therapy is a highly effective modality in the treatment of cancer. One of the severe limitations of the procedure is normal tissue tolerance to the radiation. In particular, bone marrow toxicity is the limiting factor in determining radiation dosages. In recent years, advances have been made so that it is now possible to design and create tumor-specific or tumor-related antibodies that are labeled with a radioactive substance such as $^{131}$I. See, for example, Maners et al., *Annals of Clinical and Laboratory Science*, 1988, Vol. 18, pp. 53–57.

Several $^{131}$I labeled antibodies have been prepared in attempts to maximize the localization of the radioactive material at the tumor site. Obviously, this procedure can be valuable for both therapeutic and diagnostic purposes.

For either purpose, the treatment of cancer patients with radiolabeled antibodies has been plagued by several problems. Foremost among these problems is the lack of specificity of the antibodies to the tumor. While a significant amount of the monoclonal antibody is localized at tumor cells, the amount of monoclonal antibody localized is usually only a small percentage of the total administered dose. A large amount of monoclonal antibody will, therefore, localize to the lungs, liver, spleen and bladder as well as to other organs, or exist in the circulation system until cleared by natural mechanisms.

Improved localization would greatly improve the treatment of cancer with monoclonal antibodies for two reasons: 1) It would allow an improved signal-to-noise ratio which would allow better imaging of some tumors and recognition of previously undetected tumors; and 2) It would allow a decrease in the total body irradiation and/or a decrease in a specific organ irradiation which occurs as an undesired result of the unbound or circulating monoclonal antibody.

Tumor site localization could be artificially improved by a procedure that would eliminate "circulating" monoclonal antibodies from a patient prior to the normal clearance. Advances in the development of radiolabeled delivery agents have often focused on increasing the lifetime of the agent in the patient in order to assure that the agent is given sufficient time to reach its desired location. In engineered agents which have greatly increased circulating half-lives, the ability to remove the agent from the blood stream would be even more critical.

A variety of strategies to improve tumor localization of injected labeled monoclonal antibodies have been attempted. In Sharkey et al., Cancer Research, 1988, Vol. 48, pp. 2005–2009, the authors state:

> Radiolabled antibodies have proven their usefulness in the early detection of cancer by external scintigraphic imaging.... However a major problem of radiolabeled immunodetection is the persistence of high levels of blood pooled radioactivity that increases the difficulty in identifying specific antibody accretion in tumor.

Attempts at resolving this problem are described, for example, in the following additional references: Wahl et al., Nucl. Med. Biol. 1987, Vol. 14, pp. 661–615; Wahl et al., Cancer Immunol. Immuno. Ther., 1988, Vol. 26, pp. 187–201; Begent et al.; The Lance, Oct. 2, 1982; Spies et al., Seminars in Nuclear Med., 1987, Vol. 17, pp. 267–272; Paganelli et al., Int. J. Cancer: Supplement 2, 1988, pp. 121–125; Meeker et al., Blood, 1985, Vol. 65, pp. 1349–1363; Vacca et al., Cancer, 1988, Vol. 61, pp. 58–67; and Munz et al., J. Nucl. Med., 1986, Vol. 27, pp. 1739–1745.

The therapeutic and diagnostic uses of radiolabeled monoclonal antibodies in cancer treatment is just one example of a medical agent treatment where it would be desireable to eliminate circulating levels of the medical agent more rapidly than the normal body clearance process. It need not be that the existence of the medical agent causes direct harm to a patient, but it may also be desireable in maximizing the therapeutic or diagnostic benefit hoped to be obtained from the medical agent or of another related or unrelated therapeutic or diagnostic procedure. The present invention provides an attractive and useful approached to address all of these needs.

SUMMARY OF THE INVENTION

The present invention relates to a method for removing a previously administered medical agent from a patient by passing the patient's bodily fluid containing the medical agent extracorporeally through a device which will selectively remove that medical agent from the bodily fluid. The treated bodily fluid, substantially depleted of the medical agent, is then returned to the patient.

In the preferred embodiment of the invention, the extracorporeal treatment is done in a continuous and on-line procedure rather than as a batch or bolus treatment process. Such continuous treatment is quicker, eliminates fluid balancing problems, and provides for the elimination of medical agents that are concentrated in body tissues but are in equilibrium with circulating levels of the agent.

The method incorporates the entire treatment procedure including the administration of the medical agent, and the subsequent selective extracorporeal elimination of the medical agent at a predetermined time after administration.

In one embodiment of the invention, the medical agent is a radiolabeled material that is designed to localize at or near tumor cells in a patient's body. The treatment may be performed for either therapeutic or diagnostic purposes. When used for therapeutic procedures, the radiolabeled material will irradiate the associated tumor cells to destroy or prevent growth of the tumors. When used for diagnostic procedures, the radiolabeled materials may be used for imaging tumors.

At a predetermined time after administration of the radiolabeled material or at a predetermined blood level concentration, the patient's plasma is extracorporeally passed over or through a support material. The support material will be treated so that covalently bound to the support will be some material that will act to adsorb, adsorb, immobilize, complex or in some other manner prevent passage of the radiolabeled material through the support material. The treated plasma is then returned to the patient significantly reduced in the radiolabeled material. In general, extracorporeal treatment will begin after administration of the radiolabeled material, and after substantial localization of the material to the tumor has occurred.

In a preferred embodiment, the radiolabeled material is an anti-tumor monoclonal antibody. The extracorporeal treatment will then involve passing the patient's serum through a support that has been treated to contain an antigen to the antibody. In one variant of this embodiment, the support will have an anti-species antibody covalently bound to the support material, and the monoclonal antibody will act as the antigen and be immobilized on the support bed.

In another embodiment of the invention, the medical agent is a naturally occurring compound such as an enzyme or a cytokine that is being administered for therapeutic or diagnostic purposes. In another embodiment, the medical agent is a non-naturally occurring compound or drug that is being administered for therapeutic or diagnostic purposes. Central to each embodiment of the invention is the improvement in efficacy or safety of the therapeutic or diagnostic procedure that can be gained by reducing circulating levels of the medical agent more rapidly than would occur by natural clearance of the agent via bodily systems. The safety benefits gained may be in the ability to alleviate the need for normal clearance, for example, when the circulating levels of the medical agent are not harmful, but clearance is toxic to the tissues involved in elimination, such as the kidney or liver. An example of improved efficacy is the situation where a diagnostic procedure is enhanced by elimination of circulating levels of a medical agent. Efficacy may also be found in therapeutic procedures where the elimination of circulating levels of an agent reduces non-specific toxicity and thus allows for the administration of larger doses of the beneficial medical agent.

BRIEF DESCRIPTION OF THE DRAWING

The Figure shows a schematic pathway for the utilization of the method of the present invention.

DESCRIPTION OF THE PREFERRED EMBODIMENTS

Reference will now be made in detail to the presently preferred embodiments of the invention, which, together with the following examples, serve to explain the principles of the invention.

The present invention relates to a method of treatment which comprises administering to a living being a therapeutic or diagnostic agent and thereafter extracorporeally removing a portion of said agent or a derivative thereof by passing body fluid over a chemical material adapted to selectively immobilize the agent.

The term "extracorporeal" refers to a process that occurs outside of the body of the living being that is treated. Of course, to the extent that it would be possible to treat bodily fluids as described herein—to immobilize the medical agent—within a device held physically within the body, it would also be within the scope of this invention.

The extracorporeal treatment of the present invention may be continuous, on-line treatment of the body fluid, or the treatment of one or more batch or bolus portions of the body fluid. In the preferred embodiment of the invention the treatment will be performed in a continuous or on-line manner as described below.

Therapeutic agents and diagnostic agents are referred to herein collectively as medical agents. A therapeutic agent is a medical agent administered to a patient in order to achieve an active beneficial effect on the well-being of the patient or to retard or eliminate the detrimental effects of a disease, injury, foreign invasion or the administration of other medical agents. A diagnostic agent is a medical agent that is employed to identify or quantify the extent of a medical abnormality or to assess the status of a general or specific physical trait of a patient or of the state of a specific bodily tissue or organ.

The medical agents of the present invention may be administered alone or as part of a multipart therapeutic or diagnostic procedure. The medical agent need not be the agent that directly causes the therapeutic or diagnostic benefits of the procedure utilized.

In the preferred embodiment of the invention, the method is to be performed on vertebrate animals. In a more preferred embodiment, the living beings of the invention are mammals, and in the most preferred embodiment, the living beings to be treated according to the method of this invention are human beings. Throughout this specification, the term "patient" is used interchangeably with living being.

Bodily fluids that are included and considered to be within the scope of this invention are, without limitation, blood, plasma, cerebral spinal fluid, and peritoneal fluid. In a preferred embodiment, the bodily fluid that is extracorporeally treated is blood. In the most preferred embodiment of the invention, a patient's blood is removed from the patient's body via venipuncture, plasma is isolated, and the plasma is passed over the chemical material or support that can selectively eliminate the medical agent from the serum. Plasma may be isolated via conventional procedures that generally involve either membrane or centrifugation separations of the blood into plasma and blood concentrate streams. In another preferred embodiment, the whole blood may be passed over or in proximity to a support material that will eliminate the medical agent from the blood.

The chemical material that has been adapted to selectively react with the medical agent is also referred to herein as a support or a membrane. Many materials are available which can be used for this purpose. Typically, the support is modified by covalently bonding to the material of the support a chemical compound that will complex, react with, or immobilize the medical agent.

In most cases the support material will be a porous gel or a porous membrane. Cellulose and agarose materials are commonly available for these purposes. For example, pre-activated, amine reactive cellulose is commercially available, as is oxidized amine reactive cellulose. Other materials that could be used for supports and that are susceptible to chemical modification are polyacrylonitrile, polyvinylidenedifluoride, polyvinyl alcohol, polyvinyl chloride and Nylon 66 (Immunodyne, (PALL)).

Specificity to a specific compound can usually be obtained by the use of biologically derived materials. For example, the specifity that an antibody has to its specific antigen cannot generally be duplicated by other means. Therefore, in a preferred embodiment of the present invention, the selective extracorporeal removal of medical agents from blood plasma utilizes the antibody/antigen mechanism. Typically, an antibody to the medial agent is covalently bound to a support material, and passing plasm containing the medical agent over the support will serve to remove a significant portion of the medical agent from the plasm. Of course, the process works equally well when the medical agent is an antibody and the material bounded to the support is the antigen. Certain immobilized antibodies on agarose support are commercially available (for example, from Sigma Chemical Co., St. Louis, Mo.).

Materials injected and selectively removed according to the invention may be not only antibodies, but antibody fragments, engineered peptides including with structure based on desired antibody portions, and other therapeutic or diagnostic agents, or derivatives (metabolites and complexes) thereof.

Other biologically-based selective removal mechanisms are also possible, and considered within the scope of this invention. For example, attached to the support may be antibody fragments, single chain antibodies, molecular imprinting (see Ekberg et al., Trends in Biotechnology, 1989, Vol. 7, pg. 92) molecular recognition units, heavy chain variable region gene antibodies (Ward et al., Nature, 1989, Vol. 341, pg. 544) computer designed affinity proteins, peptides or carbohydrates, and substrate and substrate analogs (for example, labeling the medical agent with heparin, and impregnating the support with heparinase or protamine).

In one embodiment of the invention, the selective removal mechanism utilizes the hapten/hapten-antibody system. In this embodiment the medical agent may be labeled with either a hapten or a hapten antibody, and the support will contain the hapten-antibody or the hapten, respectively.

In an additional embodiment of the invention, the selective removal mechanism utilizes the ligand/receptor system. An example would be the immobilization of avidin on the support material and the labeling of the medical agent with biotin. As used throughout this specification, labeling refers to binding—either covalently or by ligands—of a moiety to the medical agent that will either assist in the therapeutic or diagnostic treatment (e.g., $^{131}$I for imaging and irradiation) or will assist in the selective removal of compound or both.

In additional embodiments of the invention, the medical agents may be labeled with enzymes, toxins, drugs or radioemitting elements. The particular selective removal scheme employed will depend on the nature of the medical agent utilized, and it would be within the skill of one of ordinary skill in the art to determine which of the various schemes would be appropriate.

Of course, the medical agent of the present invention need not be labeled for either purposes of assisting in the treatment or in the selective removal procedure. For example, the medical agent may be an antibody, a hapten, a ligand or an artificial ligand, an enzyme or some other compound which can be removed selectively from solution without labeling.

Descriptions of several selective separation systems of the type contemplated by this invention are described in the following citations, each of which are incorporated herein by this reference. U.S. Pat. Nos. 4,865,841 of Balint, Jr. et al.; 4,846,786 of Freed et al.; 4,824,432 of Skurkovich et al.; 4,813,924 of Strahilevitz; 4,800,016 of Yang; 4,725,355 of Yamamoto et al.; 4,576,928 of Tani et al.; and 4,215,688 of Terman et al.

In an alternate embodiment of the invention, the selective separation system utilized is based on physico-chemical properties of the medical agent. Such mechanisms may include size occlusion, hydrophobicity, chemical reactivity, and ionic characteristics. These selection processes are generally less selective than biologically derived mechanisms, but may be beneficial in certain embodiments and are considered to be within the scope of this invention.

The medical agents of the present invention may include soluble materials such as drugs, drug/hapten complexes, drugs labeled in the ways described above, enzymes, carbohydrates, antibodies, cytokines, biological response modifier's, glycoprotiens, lipids/glycolipids, proteolipids, hormones and proteins. Partially soluble materials may also be medical agents, such as large protein complexes, liposomes, carbohydrate complexes, and inorganic complexes. Any of these compounds may be labeled either for removal purposes or for therapeutic/diagnostic purposes or may be used in their original state without additional labeling.

According to the present invention, medical agents are administered to a patient and then extracorporeally removed prior to normal clearance of the agent from the body. There are two general reasons why premature "rescue" from the medical agent may be required. First, the medical agent is beneficial to specific tissues in the body but is harmful to normal bodily tissues. This can be either acute or chronic danger, and it can be either short or long term. The harmful effect may be associated with the clearance process, or it may be associated with high circulating levels of the agent. Second, the continued presence of the medical agent in the bodily fluid may obstruct or render less effective another treatment or diagnostic action of the medical agent or another related or unrelated therapeutic or diagnostic procedure. An example of this is when the medical agent contains a radioactive label for imaging purposes. Once the tumor-specific material has accumulated at or near tumor tissue, the circulating agent can be removed from the blood stream to help clarify the image by the reduction of background. For therapeutic uses of these materials, the removal of the agent from the blood stream will allow for lower general body toxicity and can, in turn, allow for the use of higher doses of the medical agent and greater efficacy of treatment. The method of the present invention will also allow patients to fall within allowed radiation limits at earlier times for association with other individuals.

The method of the present invention has numerous advantages over other potential treatment schemes. The extracorporeal treatment can be done in a closed circuit so there will be no fluid balance issues. Agent selectivity for many systems generally is found to be excellent. In the system described in Example 1, the column is able to remove 80% of the medical agent after treatment of three plasma volumes and 90% after treatment of six plasma volumes. (A single plasma volume may be treated in about 0.5 to 1.5 hours.) Again, utilizing the system described in Example 1, after extracorporeal treatment very little blood perturbation is seen. CBC and chemistry panel of the blood remain unchanged, and less than 0.08% of human plasma proteins were removed non-specifically.

The present invention may be useful in those situations where a medical agent concentrates in a particular body tissue, and its presence in the body tissue is toxic. If the agent in the tissue is in equilibrium with the agent in a bodily fluid, treatment of the body fluid can "drive" the agent out of the tissue material.

In another embodiment of the invention, the medical agent may be an enzyme or catalatic antibody which is administered to the patient for the purpose of producing within the body an agent that acts as the therapeutic or diagnostic vehicle. Catalytic antibodies are described in Iverson et al., 1989, science, vol. 243, pp. 1184–1187.

In one preferred embodiment of the invention, the medical agent is a radiolabeled anti-tumor material. The anti-tumor material may be administered for either therapeutic or diagnostic purposes. In either mode, the agent is designed to selectively enrich the area adjacent to any tumors in the body relative to the rest of the body. When used therapeutically, the proximal radioligand will tend to destroy or impede the growth of the tumor. The concentration gradient of the agent in the vicinity of tumors allows for imaging of tumors. Such anti-tumor agents need not be radiolabeled. For example, the anti-tumor agents may include cell cytolysis factors that will destroy associated tumor cells, or they could be a bispecific antibody that binds a separately administered medical agent.

In the preferred embodiment of the invention the radio-labeled anti-tumor agent is a monoclonal antibody. Descriptions of a variety of such radiolabeled monoclonal antibodies can be found in the following references, each of which is incorporated herein by this reference: Maners et al., 1988 *Annals Of Clinical and Laboratory Science*, Vol. 18, 53–57; Ranade, 1989 *J. Clinical Pharmacol.*, Vol. 29, 873–884; Sands, 1990 *Cancer Research Suppl.* Vol. 50, 809s–813s.

A preferred separation mechanism would involve an anti-species antibody that would immobilize the labeled anti-tumor monoclonal antibody utilized. For example, and as shown in Examples 1 and 2, the monoclonal antibody is mouse HMFG (human milk fat globulin) labeled with $^{131}$I, and goat anti-mouse antibody is covalently bound to a cellulose support material.

In an additional preferred embodiment of the present invention, a radiolabeled humanized chimera antibody is the medical agent, as described in Morrison et al., Important Advances in Oncology, 1990, pp. 3–18; Colcher et al., Cancer Research, 1989, Vol. 49, pp. 1738–45, incorporated herein by reference. As seen in Example 3, an anti-idiotype antibody is immobilized on a cellulose wafer, and extracorporeal treatment is achieved.

In a further embodiment a immunoadsorption column is prepared by treatment with a hapten, benzyl diethylenetriamine pentacetic acid diamino ethane, and a radiolabeled anti-tumor anti-hapten bivalent humanized chimeric antibody is the medical agent.

The present invention has broad scope and encompasses a wide variety of applications. Based on the disclosure made herein and the knowledge of one of ordinary skill in the art, the present invention may be applied to nearly any treatment procedure with a medical agent that would benefit by the artificial clearance described herein.

According to the teachings herein, the method of the present invention would include the identification of a selective separation mechanism that would be appropriate for the selected medical agent. The separation mechanism may involve the use of an agent that will absorb, react or complex with the medical agent itself. However, it may also be more appropriate to attach the medical agent to a label that will facilitate the removal of the medical agent from the bodily fluid.

In most cases, the dynamics of the effective treatment times and the bodies clearance rates dictate that extracorporeal removal or artificial clearance of the medical agent will be initiated a short time after administration of the medical agent. A time/dose/response analysis of the beneficial and harmful effects of the medical agent will generally be available or can be obtained without undue experimentation. Based on this information, the timing for the initiation of the selective extracorporeal removal can be easily ascertained.

The Figure shows how the extracorporeal separation of the medical agent would be removed in a preferred embodiment of the invention. Blood is removed from the patient 10, via conduit 12. A blood pump 14 (generally peristaltic pumps are utilized), to facilitate removal of the blood and its further processing. The blood will pass through a plasma separator 16 where the blood is separated into plasma and plasm streams. The plasm stream will pass via conduit 18 into and through the support containing unit 20. At Junction 22, the plasma and blood concentrate streams will be remixed and flow via conduit 24 back into the patient. This is an example of a continuous, on-line extracorporeal removal system.

The following examples illustrate various presently preferred embodiments of the invention claimed herein. All papers and references cited in the examples that follow are specifically incorporated herein by reference.

EXAMPLE 1

A column to remove HMFG (human milk fat globulin) mouse antibodies, tagged with $^{131}$I from blood plasma is prepared as follows. Three disks formed of cellulose fibers, each disk almost 3 millimeters in thickness and almost 60 millimeters in diameter, with an average pore size of 20 microns, total weight of the three about 5 grams, are fitted in a polypropylene housing of size just large enough to accommodate the wafers, and with inlet and outlet conduits and distribution and collection zones respectfully associated therewith adjacent the wafer column. A piece of polyester scrim is placed over the cellulose fiber disk nearest the collection zone, to prevent bits of cellulose that break off the disks from getting through the column. The cellulose in the housing is then treated with a solution of sodium periodate (10 millimolar), sodium phosphate (to buffer, 0.015 molar), and sodium chloride (0.15 molar), adjusted to pH 6.0, for thirty minutes at a temperature of 4° C., generating aldehyde groups attached to the cellulose of the wafers at fiber surfaces.

The wafers are then treated with a recirculating solution of goat antimouse antibody (clinical grade, as sold by Medix Biotech, Incorporated, Foster City, Calif., under catalog designation V-873-03G, 1 mg antibody per milliliter of solution, at the beginning of recirculation) and sodium chloride (0.15M), adjusted to pH 7.6, for two hours at room temperature. The result is a solid state immunoaffinty column, in which the antibodies are covalently coupled in Schiff-base linkages through their protein amino groups to the aldehyde groups on the cellulose. The column is then treated, to substitute monovalent covalent linkages for the divalent, so as to be able to withstand storage, by passing through it the reducing agent sodium borohydride, in 5 millimolar solution, adjusted to pH 6.0, at room temperature, for six hours. The column now has conjugated to its cellulose about 12 milligrams of the goat antimouse antibody.

Ten milligrams of the mouse antibody above specified are injected intravenously into a patient, for radiolabeling or treating a tumor with an antigen to which binding of the mouse antibody is specific. After twenty-four hours, blood is removed through venipuncture, plasma therein separated in a membrane separator, and the plasma routed through the column. About half of the antibody injected is circulating in the blood, and 80% of this is removed in the column in 160 minutes, with almost no loss of other protein. The plasma separator used in this experiment is as found in the Century TPE (Therapeutic Plasma Exchange) device manufacture and sold by COBE Instruments, Inc. The general fluid flow is as shown in the Figure.

EXAMPLE 2

In this example, the immunoadsorption device is constructed as in Example 1, except that the starting material for the solid matrix is a commercially available preactivated cellulose capsule which preferentially immobilizes by Schiff-base covalent linkages, proteins or molecules containing amines, which are able to undergo Schiff-base linkage reactions. This capsule is commercially available from Cuno, Inc., brand named the "Zeta Affinity 60 capsule." The method for immobilizing goat antimouse heterosera antibodies to the cellulose wafers contained in this capsule is published by the manufacturer. Goat antimouse antibodies obtained from Medix Biotech, Inc. are mobilized to this cellulose matrix using the instructions supplied by the manufacturer. 35 mg of the goat antimouse heterosera are applied to the capsule, and approximately 25 mg of the goat antimouse heterosera are covalently immobilized to the cellulose matrix using this procedure.

This immunoaffinity column is then connected to the extracorporeal circuitry as described in Example 1, for use in removing radiolabeled antibodies previously administered by injection into a person.

A mouse monoclonal antibody, which binds specifically to a protein found enriched on the surfaces of some tumor cells, Human Milk Fat Globulin (HMFG) protein, is covalently labeled with a metal chelator (such as described in U.S. Pat. Nos. 4,678,667 and 4,454,106) and, further, an $^{111}$In radio nucleotide is chelated to the chelator which has been conjugated to the antibody. This antibody is then injected intravenously into a patient for the purpose of localizing to the antigen sites which are found predominately on the surfaces of tumor cells in the body, enabling a gamma camera image of that tumor by imaging the $^{111}$In radionuclide decay photons emitted from the body.

The portion of the monoclonal antibody which remains in circulation is then removed, in part, by the immunoadsorption treatment. The patient's blood is connected to the extracorporeal circuit by way of femoral vein catherization and blood is pumped via the extracorporeal system machine out of the body and through the plasma separator. Blood concentrate exiting the separator returns to the body from the separator and plasma exiting the separator passes through the immunoaffinity capsule, and further combines with the blood concentrate and returns to the patient's circulation. As the plasma generated in the extracorporeal circuit passes through the immunoaffinity column, the monoclonal antibodies are bound by the goat antimouse antibodies immobilized to the cellulose matrix surface. Two to three patient plasma volumes, at typically three liters per plasma volume, are processed in this way, over two to three hours, resulting in approximately 12 mg of monoclonal antibody being removed when 15 mg are present in the patient's blood at the beginning of the treatment.

EXAMPLE 3

A humanized chimera antibody is generated such as described, for example, by Lobuglio et al., Proc. Natl. Acad. Sci. U.S.A., 1989, Vol. 86, pp. 4220–24, and further radiolabeled with $^{131}$I in a standard radiolabeling procedure. An anti-idiotype antibody which binds specifically to the combining region of the humanized chimera is also constructed using methods as described, for example, by Rosen et al., AIDS Res. and Human Retrovinces, 1990, Vol. 6, pg. 40; and Hildreth et al., Molecular Immunology, 1989, Vol. 26, pp. 1155–67. The anti-idiotype antibody is then immobilized to the cellulose wafer as described in Example 2. The methods for use and results are the same as in Example 2.

EXAMPLE 4

An immunoaffinity column is constructed by placing 60 mm diameter round disks of porous Nylon 66 membrane (available from PALL Corp., brand named "Immunodyne") which has been surface-treated to enable covalent immobilization of amines to its surface in layers one on top of another with a nylon mesh spacer between layers in a 60 mm diameter cylindrical housing, bounded on the top and bottom by end caps which allow fluids to enter the end cap, spread over the surface of the layers, pass through each layer successively, and exit through the other end cap. While in this configuration, 10 mg of a hapten, benzyl diethylenetriamine pentaacetic acid diamino ethane is passed through the membranes and covalently bound to the membranes using the membrane manufacturer's instructions. In this way, approximately 1 microgram of hapten is immobilized per square centimeter of each layer of the immobilization membrane. For 5 layers of membrane per such device, approximately 140 micrograms of hapten are immobilized.

Five mg of radiolabeled anti-hapten, anti-tumor, bivalent humanized chimeric antibody as described by Ledoussal et al., Cancer Research, 1990, Vol. 50, pp. 3445–3452; and EP applications 369576, 369566, is injected into a patient for the purpose of localizing to tumor sites. The patient is immunoadsorbed as in Example 2, using the hapten immobilized immunoaffinity column just described, at 24 hours after the antibody was injected, and processing six plasma volumes over a period of three hours, 90% of the anti-hapten antibody is removed.

It is to be understood that the application of the teachings of the present invention to a specific medical agent and separation system will be within the capabilities of one having ordinary skill in the art in light of the teachings contained herein. Thus it will be apparent to those of ordinary skill in the art that various modifications and variations can be made in the method of the present invention. It is intended that the present invention covers these modifications and variations provided they come within the scope of the appended claimed and their equivalents.

I claim:

1. A method of therapeutic or diagnostic treatment for a living being in need thereof which comprises administering to said living being a medical agent to effect such therapeutic or diagnostic purpose and thereafter extracorporeally removing said medical agent from said living being by passing bodily fluid over a support adapted to immobilize said agent, wherein said medical agent is prematurely removed from said living being to enhance said therapeutic or diagnostic treatment, and wherein said medical agent is a radiolabeled antibody.

2. The method of claim 1 wherein said support contains anti-species antibodies.

3. A method of therapeutic or diagnostic treatment for a living being in need thereof which comprises administering to said living being a medical agent to effect such therapeutic or diagnostic purpose and thereafter extracorporeally removing said medical agent from said living being by passing bodily fluid over a support adapted to immobilize said agent, wherein said medical agent is prematurely removed from said living being to enhance said therapeutic or diagnostic treatment, and wherein said treatment is the localized therapeutic irradiation of tumor cells.

4. A method of therapeutic or diagnostic treatment for a living being in need thereof which comprises administering to said living being a medical agent to effect such therapeutic or diagnostic purpose and thereafter extracorporeally removing said medical agent from said living being by passing bodily fluid over a support adapted to immobilize said agent, wherein said medical agent is prematurely removed from said living being to enhance said therapeutic or diagnostic treatment, and, wherein said treatment is the diagnostic imaging of tumors.

* * * * *